United States Patent
Bhakoo et al.

(10) Patent No.: US 6,709,647 B2
(45) Date of Patent: *Mar. 23, 2004

(54) ANTIMICROBIAL DEODORANT COMPOSITIONS

(75) Inventors: Manmohan Bhakoo, Bebington (GB); Sally Gillian Grimshaw, Bebington (GB); Karen Anne Steele, Bebington (GB); David Taylor, Bebington (GB); Katherine Mary Thompson, Bebington (GB); David William Thornthwaite, Bebington (GB)

(73) Assignee: Unilever Home & Personal Care USA, a division of Conopco, Inc., Chicago, IL (US)

( * ) Notice: Subject to any disclaimer, the term of this patent is extended or adjusted under 35 U.S.C. 154(b) by 17 days.

This patent is subject to a terminal disclaimer.

(21) Appl. No.: 10/050,503

(22) Filed: Jan. 16, 2002

(65) Prior Publication Data

US 2003/0059396 A1 Mar. 27, 2003

(30) Foreign Application Priority Data

Jan. 16, 2001 (EP) .............................. 01300336

(51) Int. Cl.[7] .............................. A61K 7/32; A61K 7/00
(52) U.S. Cl. ........................ 424/65; 424/400; 424/401
(58) Field of Search ........................ 424/65, 400, 401

(56) References Cited

U.S. PATENT DOCUMENTS

| | | | |
|---|---|---|---|
| 4,877,605 A | 10/1989 | Hendricks | 424/65 |
| 5,153,189 A | 10/1992 | Rupp et al. | 514/211 |
| 5,188,821 A | 2/1993 | Gaffar et al. | 424/52 |
| 5,435,808 A | 7/1995 | Holzhauer et al. | 8/94.18 |
| 5,616,335 A | 4/1997 | Nicolle et al. | 424/405 |
| 5,785,957 A | 7/1998 | Losee et al. | 424/53 |
| 6,015,547 A | 1/2000 | Yam | 424/49 |
| 6,136,297 A | 10/2000 | Sagel et al. | 424/49 |
| 6,471,947 B2 * | 10/2002 | Bhakoo et al. | 424/53 |

FOREIGN PATENT DOCUMENTS

| | | |
|---|---|---|
| DE | 39 42 643 | 7/1990 |
| EP | 325 288 | 7/1989 |
| EP | 325 289 | 7/1989 |
| EP | 485 927 | 5/1992 |
| EP | 545 594 | 6/1993 |
| EP | 666 307 | 8/1995 |
| EP | 845 526 | 6/1998 |
| EP | 895 777 | 2/1999 |
| EP | 1 010 750 | 6/2000 |
| EP | 1 074 607 | 2/2001 |
| GB | 2 227 660 | 8/1990 |
| GB | 2 290 234 | 12/1995 |
| NL | 8000085 | 8/1981 |
| WO | 90/07501 | 7/1990 |
| WO | 96/05802 | 2/1996 |
| WO | 00/59461 | 10/2000 |

OTHER PUBLICATIONS

PCT International Search Report in a PCT application PCT/EP 01/15388.
Derwent Abstract of NL 8000085—pubished Aug. 3, 1981.
Partial European Search Report in an European Search Report EP 00 31 1230.
Co–pending Application: Applicant: Joiner et al., Ser. No. 10/013,602; Filed: Dec. 11, 2001.
Co–pending Application: Applicant: Bhakoo et al., Ser. No.: 10/050,970; Filed: Jan. 16, 2002.

* cited by examiner

Primary Examiner—Shelley A. Dodson
(74) Attorney, Agent, or Firm—Kevin J. Stein

(57) ABSTRACT

The present invention concerns deodorant products based on a synergistically active antimicrobial mixture of picolinic acid and a peroxyl species or equivalent source thereof. Also described is the cosmetic use of such products to treat malodour on the human body.

18 Claims, No Drawings

ANTIMICROBIAL DEODORANT COMPOSITIONS

TECHNICAL FIELD

The present invention relates to an antimicrobial deodorant composition, which is designed in particular for use on the human body. The composition is based on a synergistically active antimicrobial mixture of picolinic acid and a peroxyl species or equivalent source thereof.

BACKGROUND

It is well known that freshly secreted sweat is sterile and that body malodour is the result of biotransformation of the sweat by microorganisms living on the surface of the skin to produce volatile odoriferous compounds.

There are three types of material routinely used to combat body malodour: perfumes, antiperspirants and deodorants.

Perfumes typically work by simply masking body malodour.

Antiperspirants work by blocking the sweat glands, thereby reducing perspiration. However, even the best cosmetically acceptable antiperspirants rarely reduce sweat production by more than 50%.

Typical deodorants work by reducing the population of micro-organisms living on the surface of the skin, thereby reducing the extent of sweat biotransformation referred to above. Typical deodorants include ethanol and triclosan (2,4,4'-trichloro,2'-hydroxy-diphenyl ether). However, the antimicrobial benefit and subsequent malodour reduction obtained with such deodorants, particularly many hours after application, is not always excellent.

We have discovered that synergistic mixtures of picolinic acid and a peroxyl species or equivalent source thereof can achieve the target of providing an excellent antimicrobial benefit and subsequent malodour reduction.

Peroxyl species, in particular hydrogen peroxide and sources thereof, are well-known antimicrobial agents, although they have not been widely used in deodorant products for use on the human body. It is also known that the stability of such materials can be improved by the addition of small amounts of transition metal chelator. The use of dipicolinic acid for such purpose is described in several publications, for example EP 666,307 A (Procter and Gamble). Dipicolinic acid is also claimed to improve the antimicrobial effect hydrogen peroxide—see EP 845,526 A (Eka Chemicals).

Picolinic acid has been described in WO9007501 (Solvay Interox) as a stabiliser for percarboxylic acid bleaching compositions. The picolinic acid is added in minor amounts to sequester transition metals which catalyse peroxygen compound decomposition. Picolinic acid is also listed as an optional component for this purpose in EP 1,074,607 (Ausimont S.p.A.).

None of the prior art discloses or suggests the products of the present invention, nor the excellent antimicrobial and malodour reduction benefits obtainable by the use thereof.

SUMMARY OF THE INVENTION

We have found that use of a synergistic mixture of picolinic acid and a peroxyl species or equivalent source thereof gives an excellent antimicrobial effect and subsequent malodour reduction—much greater than that obtained from either of the two components individually. In addition, the addition of picolinic acid at such a level as to give said synergistic benefit enables less of the peroxyl species or equivalent source thereof to be used in the product—a significant benefit for products used on the human body.

Thus, in a first aspect of the invention, there is provided a deodorant product comprising picolinic acid and a peroxyl species or equivalent source thereof, characterised in that the molar ratio of picolinic acid to peroxyl species or equivalent source thereof is from 1:30 to 100:1.

In a second aspect of the present invention, there is provided a cosmetic method of gaining a deodorancy benefit on the human body comprising the use of picolinic acid and a peroxyl species or equivalent source thereof.

In a third aspect of the present invention, there is provided a method for the manufacture of a deodorant composition comprising the mixing of picolinic acid and a peroxyl species or equivalent source thereof with a cosmetically acceptable carrier material.

DETAILED DESCRIPTION OF THE INVENTION

The antimicrobial and deodorancy benefit derived from use of the present invention may be gained by independent application of picolinic acid and the peroxyl species or equivalent source thereof. Such application may be concurrent or consecutive, provided that the treated substrate experiences the presence of both components at the same time. When the components are applied from independent compositions, it is preferred that the product also comprises a means for, and/or instruction for, both of the compositions to be applied to the human body.

It is preferred that the picolinic acid and the peroxyl species or equivalent source thereof are applied from the same composition. A preferred product according to the invention is a single composition comprising both the picolinic acid and the peroxyl species or equivalent source thereof.

In most aspects of the present invention, the deodorant product is applied to the human body or to articles worn in close proximity thereto. Particularly effective malodour reduction is achieved via direct application to the human body. The greatest benefit is obtained on application to the most malodorous regions of the human body, in particular the underarm regions and the feet.

The cosmetic method of gaining a deodorancy benefit on the human body referred to in the second aspect of the present invention preferably uses the picolinic acid and the peroxyl species or equivalent source thereof at a molar ratio of from 1:30 to 100:1. This molar ratio, and that present in the deodorant product according to the first aspect of the invention, is more preferably from 1:20 to 50:1 and most preferably from 1:10 to 20:1.

Picolinic Acid

Picolinic acid is an essential component in the products of the invention. It may be used at a level of from 0.01% to 10%, particularly from 0.1% to 5%, and especially from 0.15% to 2.5%, by weight based on total weight of the composition of which it is a part. The picolinic acid may be used in its acid form or as its salt. Suitable salts include alkaline metal salts, alkaline earth metal salts, amine salts, and quaternary ammonium salts. When the picolinic acid is partially or totally in its salt form, the preferred amount is equivalent to the aforementioned preferred levels, on a molar basis.

Peroxyl Species or Equivalent Source Thereof

The products of the invention comprise a peroxyl species per se or a material that generates a peroxyl species in situ.

A peroxyl species is one that comprises a peroxy (—O—O—) group. Examples of suitable peroxyl species include hydrogen peroxide and peracids. Examples of equivalent sources thereof are compounds that produce hydrogen peroxide on dissolution in water, such as sodium perborate monohydrate, sodium perborate tetrahydrate, sodium percarbonate and percarbamide (urea-hydrogen peroxide addition compound). Further examples are enzymatic hydrogen peroxide generating systems such as peroxidases, oxidases and other oxido-reductase enzyme systems, in conjunction with their appropriate substrates. Preferred products comprise a peracid, in particular phthalimidoperoxy hexanoic acid, or a compound that produces hydrogen peroxide on dissolution in water, rather than hydrogen peroxide itself.

Particularly preferred products comprise a compound that produces hydrogen peroxide on dissolution in water, especially products from which hydrogen peroxide is absent, prior to application.

The amount of peroxyl species or equivalent source thereof in compositions of the invention may range from 0.0001% to 5%, more preferably from 0.001 to 1.5%, most preferably from 0.005% to 0.5%, by weight based on total weight of the composition of which it is a part.

Product Forms

The products of the invention may comprise compositions taking any form. When the product comprises more than one composition, it is preferred that the compositions take the same form. Example compositions include wax-based sticks, soap-based sticks, compressed powder sticks, roll-on suspensions or solutions, emulsions, gels, creams, squeeze sprays, pump sprays, and aerosols. Each product form contains its own selection of additional components, some essential and some optional. The types of components typical for each of the above product forms may be incorporated in the corresponding compositions of the invention.

Optional Additional Components

A cosmetically acceptable carrier material is a highly desired additional component of the products of the invention. The carrier material may be hydrophobic or hydrophilic, solid or liquid. Preferred carrier materials are liquids. Hydrophobic liquids suitable for use include liquid silicones, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, or additionally, non-silicone hydrophobic liquids may be used. Such materials include mineral oils, hydrogenated polyisobutene, polydecene, paraffins, isoparaffins of at least 10 carbon atoms, aliphatic or aromatic ester oils (eg. isopropyl myristate, lauryl myristate, isopropyl palmitate, diisopropyl sebecate, diisopropyl adipate, or $C_8$ to $C_{18}$ alkyl benzoates), and polyglycol ethers, for example polyglycol butanol ethers.

Hydrophilic liquid carrier materials, for example water, may also be employed.

Particularly preferred liquid carrier materials are organic solvents. A class of preferred organic solvents are aliphatic alcohols (monohydric or polyhydric, preferably having 2 to 8 carbon atoms) and polyglycol ethers, preferably oligoglycol ethers having only 2 to 5 repeat units. Examples include dipropylene glycol, glycerol propylene glycol, butylene glycol, ethanol, propanol, isopropanol, and industrial methylated spirits. The most preferred organic solvents are aliphatic alcohols, in particular those having 2 to 3 carbon atoms, especially ethanol and isopropanol.

Mixtures of carrier materials may also be used. The total amount of carrier material employed is preferably at least 5%, more preferably from 30% to 99%, and most preferably from 60% to 98% by weight of the composition, excluding any volatile propellant present.

When organic solvent is present in the composition, it is preferably present at from 30% to 98% by weight of the total weight of the liquid components of the composition; more preferably the organic solvent comprises from 60% to 97% by weight of the total liquids present.

In a particular embodiment of the invention, compositions with an organic solvent comprise a solution of the picolinic acid in said organic solvent. Such solutions are preferably homogeneous, preferably having an absorbance, relative to the solvent, of less than 0.2, especially less than 0.1 (for a 1 cm pathlength at 600 nm) measured using a Pharmacia Biotech Ultrospec 200 Spectrophotometer or similar instrument. Suitable organic solvents for use in this embodiment include alcohols having from 2 to 3 carbon atoms, especially ethanol and isopropanol. Water may also be present in such compositions.

In a further embodiment of the invention, the peroxyl species or equivalent source thereof is suspended in a hydrophobic solvent in which it is insoluble. Suitable solvents for use in this embodiment include the aforementioned liquid polyorganosiloxanes. In a preferred variation, the picolinic acid is also suspended in the liquid polyorganosiloxane in the same composition. Suspension of the peroxyl species or source thereof in a hydrophobic carrier can lead to benefits in terms of the stability of the peroxyl species or source thereof and reduced corrosion when the composition is stored in a metal container.

For some compositions, in particular those comprising sources of peroxyl species that generate hydrogen peroxide on dissolution in water, it is desired that less than 50%, in particular less than 10%, and especially less than 5% by weight of water is present as part of the liquid components of the composition.

A further particularly preferred component is an additional transition metal chelator. Whilst picolinic acid is a transition metal chelator, performance may be increased by the use of a further material of this class, in particular a material having a high binding constant for iron (III); that is to say, a binding constant for iron (III) of greater than $10^{15}$, preferably greater than $10^{20}$, and most preferably greater than $10^{26}$. A particularly preferred material of this class is diethylenetriaminepentaacetic acid (DTPA). Salts of such materials may also be employed, suitable salts being analogous to those described as suitable picolinic acid salts (vide supra). The total amount of additional transition metal chelator and salt thereof that is employed is typically from 0.1% to 5%, in particular from 0.2% to 3%, and especially from 0.4% to 2% by weight of the composition of which it is a part.

Conventional organic anti-microbial agents may also be advantageously employed in the methods and products of the present invention. Levels of incorporation are preferably from 0.01% to 3%, more preferably from 0.03% to 0.5% by weight of the composition in which they are present, excluding any volatile propellant also present. Most of the classes of agents commonly used in the art can be utilised. Preferred additional organic anti-microbials are bactericides, for example quaternary ammonium compounds, like cetyltrimethylammonium salts; chlorhexidine and salts thereof; and diglycerol monocaprate, diglycerol monolaurate, glycerol monolaurate, and similar materials, as described in "Deodorant Ingredients", S. A. Makin and M. R. Lowry, in "Antiperspirants and Deodorants", Ed. K. Laden (1999, Marcel Dekker, New York). More preferred additional anti-microbials for use in the compositions of the invention are polyhexamethylene biguanide salts; 2,4,4'-trichloro,2'-hydroxy-diphenyl ether (triclosan); and 3,7,11-trimethyldodeca-2,6,10-trienol (farnesol).

Inorganic anti-microbial agents may also be used in the compositions of the invention. Such materials can often function as anti-perspirant actives when present at a suitable concentration. Examples are often selected from astringent active salts, including, in particular, aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates. When included, preferred levels of incorporation are from 0.5% to 60%, particularly from 5% to 30% or 40% and especially from 5% or 10% to 30% or 35% by weight of a composition. Especially preferred aluminium halohydrate salts, known as activated aluminium chlorohydrates, are described in EP 6,739 (Unilever PLC and NV). Zirconium aluminium chlorohydrate actives are also preferred materials, as are the so-called ZAG (zirconium-aluminium-glycine) complexes, for example those disclosed in U.S. Pat. No. 3,792,068 (Procter and Gamble Co.). Zinc phenol sulphonate may also be used, preferably at up to 3% by weight of the composition.

Structurants and emulsifiers are further additional components of the compositions of the invention that are highly desirable in certain product forms. Structurants, when employed, are preferably present at from 1% to 30% by weight of a composition, whilst emulsifiers are preferably present at from 0.1% to 10% by weight of a composition.

Suitable structurants include cellulosic thickeners such as hydroxy propyl cellulose and hydroxy ethyl cellulose, and dibenzylidene sorbitol. Other suitable structurants include sodium stearate, stearyl alcohol, cetyl alcohol, hydrogenated castor oil, synthetic waxes, paraffin waxes, hydroxystearic acid, dibutyl lauroyl glutamide, alkyl silicone waxes, quaternium-18 bentonite, quaternium-18 hectorite, silica, and propylene carbonate. Suitable emulsifiers include steareth-2, steareth-20, steareth-21, ceteareth-20, glyceryl stearate, cetyl alcohol, cetearyl alcohol, PEG-20 stearate, dimethicone copolyol, and poloxamines.

Further emulsifiers/surfactants desirable in certain compositions of the invention are perfume solubilisers and wash-off agents. Examples of the former include PEG-hydrogenated castor oil, available from BASF in the Cremaphor RH and CO ranges, preferably present at up to 1.5% by weight, more preferably 0.3 to 0.7% by weight. Examples of the latter include poly(oxyethylene)ethers.

Certain sensory modifiers are further desirable components in the compositions of the invention. Such materials are preferably used at a level of up to 20% by weight of a composition. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, talc, finely divided silica (eg. Aerosil 200), polyethylene (eg. Acumist B18), polysaccharides, corn starch, C12–C15 alcohol benzoate, PPG-3 myristyl ether, octyl dodecanol, C7–C14 isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

Fragrance is also a desirable additional component in the compositions of the invention. Suitable materials include conventional perfumes, such as perfume oils and also include so-called deo-perfumes, as described in EP 545,556 and other publications. These latter materials may also qualify as additional organic anti-microbial agents. Levels of incorporation are preferably up to 4% by weight, particularly from 0.1% to 2% by weight, and especially from 0.7% to 1.7% by weight of a composition. Synergies can exist between the essential components of the invention and certain fragrance components—long-lasting odour control being the result.

It should be noted that certain components of compositions perform more than one function. Such components are particularly preferred additional ingredients, their use often saving both money and formulation space. Examples of such components include ethanol, isopropyl myristate, and the many components that can act as both structurants and sensory modifiers, for example silica.

Further additional components that may also be included are colourants and preservatives, for example $C_1$–$C_3$ alkyl parabens.

When the present invention involves the use of an aerosol composition, a volatile propellant is an essential component of such composition. The level of incorporation of the volatile propellant is typically from 30 to 99 parts by weight and particularly from 50 to 95 parts by weight. Non-chlorinated volatile propellant are preferred, in particular liquefied hydrocarbons or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. It is especially preferred to employ liquefied hydrocarbon gases, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane.

Other propellants that can be contemplated include alkyl ethers, such as dimethyl ether or compressed non-reactive gases such air, nitrogen or carbon dioxide.

Methods of Manufacture

Deodorant products according to the invention that are single compositions may be prepared by mixing the picolinic acid and the peroxyl species or equivalent source thereof with a cosmetically-acceptable carrier material. In a preferred method of manufacture, the cosmetically-acceptable carrier material is liquid at the temperature used for the mixing and the mixture is stirred until a homogenous dispersion or solution to be obtained.

EXAMPLES

In the following examples, comparative examples are designated by letter codes and all compositional amounts are percentages by weight of the total composition, unless otherwise indicated.

Example 1

The aerosol compositions indicated in Table 1 were prepared by methods known in the art. Their deodorancy and antimicrobial performances were tested using the following procedures.

Deodorancy Procedure

The panel employed comprised 50 individuals who had been instructed to use control ethanolic deodorant products during the week prior to the test. At the start of the test, panellists were washed with unfragranced soap and different products (1.20 g dose) applied to each axilla. (Product application was randomised to take into account any left/right bias). Panellists were instructed not to consume spicy food or alcohol, and not to wash under their own axillae, during the duration of the test. At least three expert assessors determined the intensity of axillary odour 5 hours and 24 hours after application, scoring the malodour intensity on a scale of 0–5. After each 24 hour assessment, the panellists were re-washed, and products re-applied, as above. The procedure was repeated 4 times. At the end of the test the data were analysed using standard statistical techniques.

Antimicrobial Procedure

The microbial concentrations in the axillae of the panellists were measured 24 hours after application of the products. The microbes were extracted from the axillae of the panellists using a buffered wash fluid, the resulting extract being serially diluted and then plated onto appropriate selective culture media, in order to enable enumeration of the axillary microorganisms present. After incubation at 37° C. for 2 days, the bacterial colonies were counted and the data analysed using standard statistical techniques. In Table 1, the results are expressed in terms of the numbers of colony forming units that were present per cm$^2$ of axilla extracted (logarithm to the base 10).

TABLE 1

Benefit from Aerosol Composition

| Component | Example 1 | Example A |
|---|---|---|
| Picolinic acid | 0.1 | 0 |
| Sodium perborate monohydrate | 0.2 | 0 |
| DC245[1] | 11.9 | 12.2 |
| Bentone 38 V[2] | 0.6 | 0.6 |
| Propylene carbonate | 0.2 | 0.2 |
| CAP 40[3] | 87 | 87 |
| Malodour intensity | | |
| After 5 hours | 2.19 | 2.49 |
| After 24 hours | 2.52 | 2.86 |
| Microbial numbers ($\log_{10}$cfu/cm$^2$) | | |
| Staphylococci | 4.91 | 5.87 |
| Corynebacteria | 4.14 | 5.64 |

The malodour intensity scores following treatment with Example 1 were significantly lower (at the 99% level) than those following treatment with comparative Example A, both 5 hours and 24 hours after application. Similarly, the microbial numbers observed following treatment with Example 1 were significantly lower at the 99% level.

Example 2

The aforementioned procedures were also used to assess the performance of the roll-on compositions indicated in Table 2, with the modification that a dosage of 0.30 g per axilla was employed.

TABLE 2

Benefit from Roll-on Composition

| Component | Example 2 | Example B |
|---|---|---|
| Picolinic acid | 0.1 | 0 |
| Sodium perborate monohydrate | 0.2 | 0 |
| Klucell 99M | 0.65 | 0.65 |
| Absolute ethanol | 60 | 60 |
| Deionised water | 39.05 | 39.35 |
| Malodour intensity | | |
| After 5 hours | 1.80 | 2.17 |
| After 24 hours | 2.24 | 2.50 |

TABLE 2-continued

Benefit from Roll-on Composition

| Component | Example 2 | Example B |
|---|---|---|
| Microbial numbers ($\log_{10}$cfu/cm$^2$) | | |
| Staphylococci | 5.38 | 5.84 |
| Corynebacteria | 4.54 | 5.39 |

The malodour intensity scores following treatment with Example 2 were significantly lower (at the 99% level) than those following treatment with comparative Example B, both 5 hours and 24 hours after application. Similarly, the microbial numbers observed following treatment with Example 2 were significantly lower at the 99% level.

Example 3

This Example demonstrates the ability of a peracid, phthalimidoperoxy hexanoic acid (PAP), to act as the peroxyl species and give a strong synergistic antimicrobial effect with picolinic acid.

A cell suspension of *Staphylococcus epidermidis* in 50 mM MES buffer (2-[N-morpholino]ethanesulfonic acid, Sigma M5287) was prepared to an OD$_{600}$ nm of 0.022 and equal portions were treated with the components indicated in Table 3, to give the weight percentages also indicated. Samples were removed immediately and after 60 minutes; said samples being decimally diluted in a quench solution (vide infra) and then plated onto a suitable culture medium. The plates were incubated at 37° C. for 48 hours, then read and the bacterial numbers calculated.

TABLE 3

Benefit from Picolinic Acid + PAP

| Component(s)[1] | Example C[2] | Example D | Example E | Example 3 |
|---|---|---|---|---|
| Picolinic acid | 0 | 0.12 | 0 | 0.12 |
| PAP | 0 | 0 | 0.02 | 0.02 |
| Bacterial no.[3] | | | | |
| Immediate | 6.45 | 6.60 | 6.47 | 6.53 |
| After 60 mins. | 6.45 | 6.50 | 6.50 | 2.58 |

[1]In solution in 50 mM MES at pH 6.5.
[2]Example C comprised solely MES buffer at pH 6.5.
[3]Log$_{10}$cfu/ml of the test suspension.

The quench solution used was a solution of:

| Tween 80 | 3% w/v |
| Lecithin | 0.24% w/v |
| Sodium thiosulphate | 0.5% w/v | in 37.5 mM phosphate buffer, at pH 7.9, containing 0.05% v/v Triton X-100 (iso-octyl phenoxy polyoxyethanol).

The amounts of picolinic acid and PAP in Example 3 equate to a molar ratio of 13.6:1. The great reduction in bacterial numbers found with Example 3 indicates the strong synergy between the components.

Examples 4 and 5

An analogous experiment to that performed with Example 3 was performed with the components indicated in Table 4. In this Table, the amounts indicated are milliMolar concentrations and the antimicrobial effect is expressed in terms of the reduction in bacterial numbers achieved.

TABLE 4

Synergistic Effect of Picolinic Acid + Perborate

| Component(s)[1] | Example F | Example G | Example 4 | Example H | Example 5 |
|---|---|---|---|---|---|
| Picolinic acid | 5 | 0 | 5 | 0 | 5 |
| Perborate.$H_2O$ | 0 | 2 | 2 | 0 | 0 |
| Perborate.4 $H_2O$ | 0 | 0 | 0 | 0.5 | 0.5 |
| Reduction in bacterial no.[2] | <2.59 | <2.59 | 5.06 | <2.59 | 5.54 |

[1]In solution in 50 mM MES at pH 6.5. The perborates used were sodium salts.
[2]$Log_{10}$cfu/ml of *S. epidermidis* (as with Example 3).

The results of Table 4 illustrate the strong synergy between picolinic acid and perborate at molar ratios of 2.5:1 and 10:1.

Examples 6 and 7

An analogous experiment to that performed with Example 3, with the modification of using Corynebacteria rather than *S. epidermidis*, was performed with the components indicated in Table 5. In this Table, the amounts indicated are milliMolar concentrations and the effect is expressed as in Table 3.

TABLE 5

| | Example | | | | | |
|---|---|---|---|---|---|---|
| Component(s)[1] | I | J | K | 6 | L | 7 |
| Picolinic acid | 0 | 2.5 | 0 | 2.5 | 0 | 2.5 |
| Hydrogen peroxide | 0 | 0 | 0.5 | 0.5 | 0 | 0.5 |
| DTPA[2] | 0 | 0 | 0 | 0 | 10 | 10 |
| Bacterial no.[3] | | | | | | |
| Immediate | 5.9 | 6.1 | 6.1 | 6.3 | 6.0 | 5.9 |
| After 60 mins. | 5.6 | 6.0 | 4.6 | 3.0 | 5.9 | 2.0 |

[1]In solution in 50 mM MES at pH 6.5.
[2]Diethylenetriaminapentaacetic acid.
[3]$Log_{10}$cfu/ml of Corynebacteria.

The results of Table 5 illustrate the synergy between picolinic acid and hydrogen peroxide and the further improvement in performance with the inclusion of DTPA.

Examples 8 to 10

Analogous experiments to that performed with Example 3 were also performed with the components indicated in Tables 6 and 7. In these Tables, the amounts indicated are milliMolar concentrations and the antimicrobial effect is expressed in terms of the concentration of bacteria remaining after 60 minutes.

TABLE 6

Synergistic Effect of Picolinic Acid + Percarbonate

| | Example | | | | |
|---|---|---|---|---|---|
| Component(s)[1] | M | N | 8 | O | 9 |
| Picolinic acid | 0 | 0 | 5 | 0 | 5 |
| Percarbonate | 0 | 0.5 | 0.5 | 0.1 | 0.1 |
| Bacterial no.[2] | 6.39 | 6.13 | 11.30 | 6.39 | 4.29 |

[1]In solution in 50 mM MES at pH 6.5. The percarbonate used was the sodium salt.
[2]$Log_{10}$cfu/ml of *S. epidermidis* (as with Example 3).

The results of Table 6 illustrate the strong synergy between picolinic acid + percarbonate at molar ratios of 10:1 and 50:1.

TABLE 7

Comparison with Dipicolinic Acid + Hydrogen Peroxide

| Component(s)[1] | Example P | Example Q | Example 10 |
|---|---|---|---|
| Picolinic acid | 0 | 0 | 2.5 |
| Dipicolinic acid | 0 | 2.5 | 0 |
| Hydrogen peroxide | 0 | 0.25 | 0.25 |
| Bacterial no.[2] | 6.15 | 6.02 | 3.32 |

[1]In solution in 50 mN MES at pH 6.5.
[2]$Log_{10}$cfu/ml of *S. epidermidis* (as with Example 3).

The results of Table 7 illustrate the much greater effect of picolinic acid in combination with hydrogen peroxide than dipicolinic acid in combination with hydrogen peroxide.

Examples 11 to 22

The compositions shown in Tables 8 to 11 may be prepared by methods common in the art.

TABLE 8

Squeeze Spray Compositions

| Component | Example 11 | Example 12 | Example 13 |
|---|---|---|---|
| Ethanol | 60 | 70 | 75 |
| Picolinic acid | 0.2 | 0.1 | 0.1 |
| Sodium perborate.$H_2O$ | 0.1 | 0.1 | 0.2 |
| DTPA | 0 | 0.5 | 1.0 |
| Sodium hydroxide | Sufficient to neutralise the DTPA | | |
| Fragrance | 1.2 | 1.3 | 1.2 |
| Glycerol | 1.0 | 1.0 | 1.0 |
| Water | To 100 | To 100 | To 100 |

TABLE 9

Further Roll-on Compositions

| Component | Example 14 | Example 15 | Example 16 |
|---|---|---|---|
| Ethanol | 55 | 60 | 65 |
| Picolinic acid | 0.5 | 0.5 | 0.2 |
| Sodium percarbonate | 0.05 | 0.1 | 0.05 |
| DTPA | 1.0 | 0 | 0 |
| Sodium hydroxide | 0.34 | 0 | 0 |
| Fragrance | 1.4 | 1.4 | 1.4 |
| Klucel M | 0.65 | 0.65 | 0.65 |
| Water | To 100 | To 100 | To 100 |

TABLE 10

Solid Compositions

| Component | Example 17 (Soft Solid) | Example 18 (Gel Stick) |
| --- | --- | --- |
| Picolinic acid | 0.3 | 0.2 |
| Sodium perborate.4H$_2$O | 0.1 | 0.1 |
| Perfume | 1.0 | 1.2 |
| Dextrin Palmitate | 10 | 0 |
| Finsolv TN[1] | To 100 | 0 |
| Propylene Glycol | 0 | 22.5 |
| Dipropylene Glycol | 0 | 40.0 |
| Sodium Stearate | 0 | 5.5 |
| Tetronic 1307[2] | 0 | 3.0 |
| Water | 0 | To 100 |

[1]C12–C15 alkyl benzoate, ex Finetex.
[2]Poloxamine 1307, ex BASF.

TABLE 11

Further Aerosol Compositions

| | Example | | | |
| --- | --- | --- | --- | --- |
| Component | 19 | 20 | 21 | 22 |
| Picolinic acid | 1.0 | 1.0 | 0.6 | 0.2 |
| PAP[1] | 0.1 | 0.2 | 0.1 | 0.1 |
| Isopropyl myristate | 0.33 | 0.33 | 0.33 | 0.33 |
| Water | 2.55 | 2.56 | 2.55 | 2.55 |
| CAP40 | 35 | 45 | 55 | 55 |
| Ethanol | To 100 | To 100 | To 100 | To 100 |

[1]Phthalimidoperoxy hexanoic acid.

What is claimed is:

1. A deodorant product comprising picolinic acid and a peroxyl species or equivalent source thereof, wherein the molar ratio of picolinic acid to peroxyl species or equivalent source thereof is from 1:30 to 100:1.

2. A deodorant product as in claim 1, comprising a single composition comprising both the picolinic acid and the peroxyl species or equivalent source thereof.

3. A deodorant product as in claim 1, wherein the peroxyl species or equivalent source thereof is a peracid or a compound that produces hydrogen peroxide on dissolution in water.

4. A deodorant product according to claim 1, comprising an additional transition metal chelator.

5. A deodorant product according to claim 4, wherein the transition metal chelator has a binding coefficient for iron (III) of greater than $10^{15}$.

6. A deodorant product according to claim 5, wherein the transition metal chelator is diethylenetriaminepentaacetic acid.

7. A deodorant product according to claim 1, wherein the molar ratio of picolinic acid to peroxyl species or equivalent source thereof is from 1:10 to 20:1.

8. A deodorant product according to claim 1, wherein the picolinic acid is present at a level from 0.01% to 10% by weight of the composition of which it is a part.

9. A deodorant product according to claim 8, wherein the picolinic acid is present at a level from 0.15% to 2.5% by weight of the composition of which it is a part.

10. A deodorant product according to claim 1, wherein the peroxyl species or equivalent source thereof is present at a level from 0.0001% to 1.5% by weight of the composition of which it is a part.

11. A deodorant product according to claim 10, wherein the peroxyl species or equivalent source thereof is present at a level from 0.003% to 0.5% by weight of the composition of which it is a part.

12. A deodorant product according to claim 1, comprising a cosmetically acceptable carrier material.

13. A cosmetic method of gaining a deodorancy benefit on the human body comprising the use of picolinic acid and a peroxyl species or equivalent source thereof.

14. A cosmetic method according to claim 13, wherein the picolinic acid and the peroxyl species or equivalent source thereof are used at a molar ratio of from 1:30 to 100:1.

15. A cosmetic method according to claim 13, wherein the picolinic acid and the peroxyl species or equivalent source thereof are applied from the same composition, said composition comprising a cosmetically acceptable carrier material.

16. A cosmetic method according to claim 13, comprising the use of an additional transitional metal chelator.

17. A cosmetic method according to claim 16, comprising the use of diethylenetriaminepentaacetic acid.

18. A method for the manufacture of a deodorant composition comprising the mixing of picolinic acid and a peroxyl species or equivalent source thereof with a cosmetically acceptable carrier material.

* * * * *